US010702186B2

(12) United States Patent
Amies et al.

(10) Patent No.: US 10,702,186 B2
(45) Date of Patent: Jul. 7, 2020

(54) METHOD AND APPARATUS FOR IDENTIFYING AN ORGAN STRUCTURE OF AN EXAMINED OBJECT IN MAGNETIC RESONANCE IMAGE DATA

(71) Applicant: Siemens Healthcare GmbH, Erlangen (DE)

(72) Inventors: Christopher Jude Amies, Pleasant Hill, CA (US); Arne Hengerer, Moehrendorf (DE); Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 499 days.

(21) Appl. No.: 15/370,062

(22) Filed: Dec. 6, 2016

(65) Prior Publication Data
US 2018/0153431 A1    Jun. 7, 2018

(51) Int. Cl.
*A61B 5/055* (2006.01)
*G01R 33/56* (2006.01)
(Continued)

(52) U.S. Cl.
CPC .......... *A61B 5/055* (2013.01); *G01R 33/4818* (2013.01); *G01R 33/543* (2013.01);
(Continued)

(58) Field of Classification Search
CPC ... A61B 5/055; A61B 5/7257; A61B 2576/00; G01R 33/4818; G01R 33/543;
(Continued)

(56) References Cited

U.S. PATENT DOCUMENTS 6,230,040 B1 *  5/2001  Wang ................. G01R 33/4822
                                                          324/309
2001/0033162 A1 * 10/2001  Harvey ............... G01R 33/561
                                                          324/307
(Continued)

FOREIGN PATENT DOCUMENTS

CN    101201392 A    6/2008
CN    101305908 A    11/2008
CN    101680938 A    3/2010

OTHER PUBLICATIONS

Kim, et al. "Edge detection using sub-sampled k-space data: application to upper airway MRI" Proceedings of the International Society for Magnetic Resonance in Medicine, 15th Annual Meeting and Exhibition, Berlin, Germany, May 19-25, 2007 vol. 15, p. 3458, (2007).
Konar, et al. "Region of interest compressive sensing (ROICS)" Proceedings of the International Society for Magnetic Resonance in Medicine, 21st Annual Meeting and Exhibition, Salt Lake City, Utah, USA, April 20-26, 2013, vol. 21, p. 3801, (2013).
(Continued)

*Primary Examiner* — Amelie R Davis
*Assistant Examiner* — John Denny Li
(74) *Attorney, Agent, or Firm* — Schiff Hardin LLP

(57) ABSTRACT

In a method and apparatus for identifying an organ structure of an examined object in magnetic resonance image data, magnetic resonance measurement data for the organ structure of the examined object are acquired by operation of a magnetic resonance scanner using a magnetic resonance sequence that specifies a sampling scheme of k-space. Magnetic resonance image data are reconstructed from the magnetic resonance measurement data. The organ structure is identified in the magnetic resonance image data. The sampling scheme of k-space is selected so as to support the subsequent identification of the organ structure in the magnetic resonance image data reconstructed from the magnetic resonance measurement data.

11 Claims, 3 Drawing Sheets

(51) Int. Cl.
*G01R 33/48* (2006.01)
*G01R 33/54* (2006.01)
*A61B 5/00* (2006.01)
*A61N 5/10* (2006.01)
*G01R 33/58* (2006.01)

(52) U.S. Cl.
CPC ........ *G01R 33/5608* (2013.01); *A61B 5/7257* (2013.01); *A61B 2576/00* (2013.01); *A61N 5/1039* (2013.01); *A61N 2005/1055* (2013.01); *G01R 33/4824* (2013.01); *G01R 33/583* (2013.01)

(58) Field of Classification Search
CPC .............. G01R 33/5608; G01R 33/824; G01R 33/583; G01R 33/4826; A61N 5/1039; A61N 2005/1055
See application file for complete search history.

(56) References Cited

U.S. PATENT DOCUMENTS

| | | | |
|---|---|---|---|
| 2007/0043286 A1* | 2/2007 | Lu | A61N 5/103 600/407 |
| 2008/0116892 A1 | 5/2008 | Laub et al. | |
| 2008/0285833 A1 | 11/2008 | Fu et al. | |
| 2010/0189328 A1* | 7/2010 | Boernert | G01R 33/56375 382/131 |
| 2015/0343237 A1 | 12/2015 | Hausotte et al. | |
| 2016/0059041 A1 | 3/2016 | Grodzki et al. | |
| 2016/0086330 A1 | 3/2016 | Grodzki et al. | |

OTHER PUBLICATIONS

Chinese Office Action dated Sep. 29, 2019, for Application No. 201711261863.4, and English translation.

* cited by examiner

METHOD AND APPARATUS FOR IDENTIFYING AN ORGAN STRUCTURE OF AN EXAMINED OBJECT IN MAGNETIC RESONANCE IMAGE DATA

BACKGROUND OF THE INVENTION

Field of the Invention

The invention relates to a method for identifying an organ structure of an examined object in magnetic resonance image data, as well as a magnetic resonance apparatus, and a data storage medium for implementing such a method.

Description of the Prior Art

In a magnetic resonance apparatus, also referred to as a magnetic resonance tomography system, the body to be examined, of an examined object, for example of a patient, a healthy volunteer, an animal or a phantom, is usually exposed with the use of a basic field magnet to a relatively high basic magnet field, of 1.5 or 3 or 7 tesla for example. Additionally, gradient switching is activated with the use of gradient coils. Via a radio-frequency antenna, radio-frequency pulses, for example excitation pulses, are omitted that result in the nuclear spins of certain atoms being excited in a resonant manner by these radio-frequency pulses so as to be tilted over by a defined flip angle with respect to the magnetic field lines of the basic field. During relaxation of the nuclear spins, radio-frequency signals, so-called magnetic resonance signals, are emitted that are received by suitable radio-frequency antennas, which then undergo further processing. The desired image data can be reconstructed from the raw data acquired in this way.

For a specific measurement, therefore, a specific magnetic resonance sequence, also referred to as a pulse sequence, must be emitted overall, composed of a succession of radio-frequency (RF) pulses, for example excitation pulses and refocusing pulses, and gradient switchings that are activated appropriately coordinated with the RF pulses in various gradient axes along various spatial directions. Appropriately timed, read-out windows are set that specify the time periods during which the induced magnetic resonance signals are captured.

Furthermore, various options are known for identifying an organ structure in magnetic resonance image data that are reconstructed from such magnetic resonance measurement (raw) data acquired by such a magnetic resonance scanner. In this regard, the organ structure can be an entire body organ of the examined object or a part of an organ of the examined object. In addition to manual segmentation, various semi-automatic or automatic segmentation methods are known for identifying the organ structure in the magnetic resonance image data. Regardless of the method used for identifying the organ structure, the outcome or the quality of the identification of the organ structure is typically dependent on the image quality of the magnetic resonance image data. A high level of image quality will typically result in a robust identification of the organ structure.

The identification of an organ structure in magnetic resonance image data can be needed for planning a radiation treatment of the examined object or patient, for example. During a radiation treatment, target tissue of a patient, such as a tumor, is irradiated with ionizing radiation. In this regard, external radiotherapy is well-known, wherein the radiation originates from outside the body. Internal radiotherapy, also referred to as brachytherapy, is likewise well-known.

In the magnetic resonance image data, usually the target volume of the radiation treatment is defined first, and the surrounding tissue to be spared, for example neural tissue is localized. As the target organ, the identified organ structure can serve in this way as the basis for defining the precise target volume of the radiation treatment. Also, as the at-risk organ, the identified organ structure can serve as the basis for defining the tissue to be spared. The identified organ structure can also be included in a calculation of an electron density map, which serves as the basis of a dose calculation for planning the radiation treatment.

In addition to computed tomography image data, magnetic resonance image data are being increasingly employed for planning s radiation treatment, because since magnetic resonance image data have a better soft tissue contrast and in this manner enable better identification of target organs and/or at-risk organs. Furthermore, in a development of the last few years called exclusively magnetic resonance-based radiation treatment planning ("MR-only RT Planning", MRORTP), computed tomography image data are eliminated from the planning process in suitable clinical applications. In this manner, radiation treatment planning should be effected exclusively on the basis of magnetic resonance image data acquired from the patient. In this way for example, the quantity of necessary patient images (only magnetic resonance images in place of computed tomography images and magnetic resonance images) can be reduced and/or possible registration errors between the CT image data and magnetic resonance image data avoided.

US 2016/0059041 A1 describes an MR-based method to monitor radiation therapy of a patient. US 2015/0343237 A1 describes using MR-data in order to determine a target region for radiotherapy. US 2016/0086330 A1 describes determining periodic movement of a tumor on the basis of 4D MRI images in order to compile a more efficient treatment plan.

SUMMARY OF THE INVENTION

An object of the invention is to enable an improved identification of an organ structure of an examined object in magnetic resonance image data.

The inventive method for identifying an organ structure of an examined object in magnetic resonance image data has the following method steps. Magnetic resonance measurement data for the organ structure of the examined object are acquired by the operation of a magnetic resonance apparatus (i.e., the scanner thereof) using a magnetic resonance sequence that specifies a sampling scheme in k-space. Magnetic resonance image data are reconstructed from the magnetic resonance measurement data. The organ structure is identified in the magnetic resonance image data. The sampling scheme in k-space is specifically selected/designed to as to support the subsequent identification of the organ structure in the magnetic resonance image data reconstructed from the magnetic resonance measurement data.

The magnetic resonance measurement data are typically captured by applying phase coding gradients and frequency coding gradients and recording the resulting magnetic resonance signals with a radio-frequency coil. The magnetic resonance signals read out during capture of the magnetic resonance measurement data are typically entered into a memory at data entry points, called k-space. In this context, k-space can be considered as a spatial frequency domain.

During acquisition of the magnetic resonance measurement data, k-space is usually filled (sampled) by the use of a deterministic sampling scheme that is specified by the magnetic resonance frequency. In this way, the magnetic resonance measurement data are typically just the raw data representing the magnetic resonance signals recorded in the spatial frequency domain. The magnetic resonance measurement data are therefore not typically directly available to a diagnostician for the purpose of making a medical diagnosis.

Instead, magnetic resonance image data are reconstructed from the magnetic resonance measurement data, which image data can be presented on a display unit and/or can be made available to a competent person for establishing a diagnosis. In this regard, reconstruction of the magnetic resonance image data from the magnetic resonance measurement data includes the generation of magnetic resonance images in the image domain from the magnetic resonance signals in k-space. The reconstruction of the magnetic resonance image data can be accomplished by methods that are well known to those skilled in the art, for example via a Fourier transform.

Identification of the organ structure involves an automatic, semi-automatic or manual recognition of the organ structure in the magnetic resonance image data. The identification of the organ structure can be a determination that is made based on a part of the magnetic resonance image data being attributable to the organ structure. In this manner, the identification of the organ structure involves defining, for each voxel in the magnetic resonance image data, whether that voxel belongs to the organ structure or not. Automatic or semi-automatic identification of the organ structure can include a segmentation of the organ structure by the use of a segmentation algorithm. Such a segmentation algorithm can make use of known segmentation techniques, for example an active contours segmentation method (e.g. active snakes), a level-set segmentation method, a region growing segmentation method, or a statistical segmentation method (e.g. active shape models). In the case of semi-automatic segmentation, the user can initialize the segmentation, for example by setting a seed point and/or by setting at least one landmark. The user can also monitor and/or change the ongoing segmentation. Identification of the organ structure can also involve contouring of the organ structure, especially in the context of planning a radiation treatment of the examined object. In this regard, the contouring can be effected with the support of automatic image processing methods for the magnetic resonance image data.

The identified organ structure is provided in electronic form as an output from the processor in which the identification was implemented, via an output interface such as a display monitor, and/or stored in a database. Alternatively or additionally, the identified organ structure can be passed to a further processing unit that can carry out further processing of the magnetic resonance image data based on the identified organ structure. In the case of planning a radiation treatment of the examined object, the identified organ structure can be set as the target organ or at-risk organ for the radiation treatment planning.

The inventive procedure is based on coordinating the sampling scheme of k-space with the subsequent identification of the organ structure. In this way, acquisition of the magnetic resonance measurement data can be optimized such that the organ structure can be identified particularly simply or precisely in the magnetic resonance image data reconstructed from the magnetic resonance measurement data. The magnetic resonance measurement data are preferably entered in k-space in such a manner that the organ structure can be segmented and/or contoured particularly simply or precisely in the magnetic resonance image data reconstructed from the magnetic resonance measurement data. The sampling scheme of k-space can be coordinated specifically to the organ structure to be identified. The magnetic resonance sequence employed for the purpose of acquiring the magnetic resonance measurement data can specify a sampling scheme that results in particularly suitable magnetic resonance measurement data for the subsequent identification of the organ structure. Alternatively or additionally, the sequence can specify to be used as settings for the execution of the magnetic resonance sequence by the scanner, so that the sampling scheme generates particularly suitable magnetic resonance measurement data for the subsequent identification of the organ structure based on the parameters.

The sampling scheme can be set dependent on preliminary magnetic resonance measurement data acquired in a preliminary measurement effected prior to the acquisition of the diagnostic magnetic resonance measurement data. The preliminary measurement can be implemented, for example, in the form of a localizer measurement or an auto-align measurement. Advantageously, the magnetic resonance preliminary measurement data already includes measurement data from the organ structure of the examined object.

Identification of the organ structure can be implemented by a recognition of an outer contour of the organ structure in the magnetic resonance image data. In this regard, the outer contour of the organ structure can represent an outer boundary of the organ structure with respect to the surrounding tissue. The outer contour of the organ structure can therefore also be designated as the outline or profile or outer limit or outer line of the organ structure. By recognizing the outer contour of the organ structure, it is possible to define particularly simply which part of the magnetic resonance image data is attributable to the organ structure. The sampling scheme therefore can support identification of the organ structure in a manner such the sampling scheme supports recognition of the outer contour of the organ structure in the magnetic resonance image data. In this manner, the sampling scheme is realized such that the outer contour of the organ structure is presented in an emphasized manner or is easily recognizable in the magnetic resonance image data reconstructed from the magnetic resonance measurement data. In this manner, the sampling scheme can be designed specifically for measurement of the outer contour of the organ structure. Thus, a direct visualization of the outer organ contour can be present in the magnetic resonance image data. This can then be used for identification of the organ structure. An internal structure of the organ structure can naturally be visible additionally in the magnetic resonance image data reconstructed from the magnetic resonance measurement data. Options for configuring the sampling scheme to simplify recognition of the outer contour of the organ structure are described in the embodiments.

The magnetic resonance image data acquired by the inventive procedure can be employed particularly advantageously for the planning of a radiation treatment of the examined object. An especially rapid and/or simple and/or precise identification of the organ structure in the magnetic resonance image data is possible. The identified organ structure can be used as the target organ or at-risk organ for planning the radiation treatment of the examined object. The inventive procedure thus can improve the contouring of the organ structure that is needed for the subsequent planning of the radiation treatment. Automation of the contouring of the organ structure can also be supported advantageously in this way. In this manner, a user-independent or standardized contouring of the organ structure can be achieved.

The inventive procedure also can enable a particularly simple modeling of a movement of the organ structure if the magnetic resonance image data maps the organ structure in a time-resolved manner. In this manner, the sampling scheme can be optimized for tracking the outer contour of the organ structure in the magnetic resonance image data over the period of acquisition of the magnetic resonance measurement data. To this effect, a 4D cine magnetic resonance sequence can be employed for acquisition of the magnetic resonance measurement data for example. Where the outer contour of the organ structure can be identified in a time-resolved manner, movement correction of the magnetic resonance image data can be employed for example. Deployment in adaptive radiotherapy is also conceivable, particularly in the case of use in a hybrid magnetic resonance radiation treatment unit, where the magnetic resonance measurement data is acquired from the examined object and the examined object is treated with radiation in the same session. Optimization of the sampling scheme therefore allows improved tracking of the volume of the organ structure in the magnetic resonance image data, for example compared with the use of navigator techniques, to be enabled.

In an embodiment, the sampling scheme of k-space supports the subsequent identification of the organ structure by providing for a higher sampling density in an outer region of k-space than in a central region of k-space.

In particular, k-space is subdivided in to a central region and an outer region, wherein the outer region surrounds the central region. The central region of k-space comprises in particular a center of k-space. In this manner, magnetic resonance measurement data is deposited in the central region of k-space, which data corresponds to lower spatial frequencies than the magnetic resonance measurement data deposited in the outer region of k-space.

The fact that the sampling scheme of k-space provides for a higher sampling density in the outer region of k-space than in the central region of k-space means that in the outer region, the sampling points are situated more densely than in the central region. As described more precisely in the next embodiment, it is also possible for no sampling at all to be effected in the central region of k-space. Alternatively, it is also conceivable for the entirety of k-space to be sampled uniformly and to use the sampling points from the outer region of k-space exclusively or primarily for reconstruction of the magnetic resonance image data.

The magnetic resonance measurement data entered in the outer region of k-space, which corresponds to the high spatial frequencies, are typically responsible for sharpness information or edge information in the reconstructed magnetic resonance image data. Consequently, an increased (more dense) sampling of k-space in the outer region can advantageously result in an emphasis of the outer contours of the organ structure in the magnetic resonance image data reconstructed from the magnetic resonance measurement data. This allows the organ structure in the magnetic resonance image data acquired in this way to be identified particularly simply. A higher sampling density in the central region than in the outer region of k-space is usually present in conventional undersampling methods.

In another embodiment, the sampling scheme of k-space provides for sampling of k-space exclusively in the outer region.

In this manner, no sampling whatsoever of k-space occurs in the central region of k-space. Thus, only the higher spatial frequencies in k-space are sampled. In this manner, the outer contour of the organ structure in the magnetic resonance image data can be emphasized particularly clearly so that identification of the organ structure can be effected particularly simply. The boundary between the central region and the outer region in k-space can be set in consideration of the spatial sharpness needed for identifying the organ structure.

In another embodiment, the sampling scheme of k-spaces provides for a spiral or radial sampling of k-space with a higher sampling density in the outer region than in the central region.

It is also conceivable for the spiral or radial sampling of k-space to be effected exclusively in the outer region. In this manner, for example, one outer arc of a spiral can be sampled exclusively for acquisition of the magnetic resonance measurement data. In the present case, the spiral or radial sampling means that a time saving and/or reduction in movement artifacts can additionally be achieved.

In another embodiment, the higher sampling density in the outer region than in the central region results in an emphasizing of an outer contour of the organ structure in the reconstructed magnetic resonance image data, and the identification of the organ structure is effected using the emphasized outer contour of the organ structure in the magnetic resonance image data.

The emphasized outer contour of the organ structure can markedly simplify segmentation or contouring of the organ structure. In this manner, the organ structure can thus be identified particularly advantageously in the magnetic resonance image data.

In a further embodiment, the sampling scheme of k-space is determined based on training magnetic resonance image data, which have been acquired from at least one subject other than the examined object, and the organ structure of the at least one subject is already present and identified in the training magnetic resonance image data.

The training magnetic resonance image data can have been captured similarly to the diagnostic magnetic resonance image data and stored in an atlas. The training magnetic resonance image data are preferably acquired from a number of subjects other than the examined object so that a larger population basis underlies the training magnetic resonance image data. In particular, a manual identification such as contouring of the organ structure of the at least one subject, possibly with the aid of automatic image processing techniques, is effected. Naturally, the same organ structure that is to be identified in the concrete case is in particular already present and identified in the training magnetic resonance image data. Furthermore, parameters of the sampling scheme used in each case for acquisition of the training magnetic resonance image data can be deposited with respect to the training magnetic resonance image data.

The organ structure already present and identified in the training magnetic resonance image data can be a valuable basis for determination of the sampling scheme. In this manner, the sampling scheme can be tailored particularly suitably to identification of the organ structure. An advantageous procedure in this regard is described in the next embodiment.

In this embodiment, the sampling scheme of k-space is determined based on the training magnetic resonance image data by calculating a sampling mask based on an outer contour of the organ structure of the at least one subject identified in the training magnetic resonance image data. The sampling scheme of k-space causes k-space to be sampled according to the sampling mask in a manner such that an outer contour of the organ structure of the examined object is emphasized in the reconstructed magnetic resonance image data. The identification of the organ structure of the examined object is effected using the emphasized outer contour of the organ structure of the examined object in the magnetic resonance image data.

In this manner, based on the organ structure already identified in the training magnetic resonance image data, it is possible to determine a specific pattern of how the organ structure to be identified or its outer contour appears in k-space. This specific pattern, which can also be designated as the fingerprint or signature of the organ structure to be identified in the spatial frequency domain, can then provide the basis for definition of the sampling mask. In this manner, the sampling scheme can be tailored particularly suitably to identification of the organ structure.

The sampling mask can define a region in k-space that includes those relevant spatial frequencies that have to be sampled so that the outer contour of the organ structure of the examined object is emphasized in the reconstructed magnetic resonance image data. To determine the sampling mask, a frequency analysis is carried out, in particular of the outer contour of the organ structure of the at least one subject identified in the training magnetic resonance image data. The sampling mask can then be set as the spatial frequency pattern in k-space that, when sampled (filled with data) results in representation of the outer contour of the organ structure in the magnetic resonance image data reconstructed from the magnetic resonance measurement data.

A specific example of this embodiment is as follows.

A number of training magnetic resonance image datasets, which represent in each case the organ structure from various subjects, are used as input parameters to a processor. In these training magnetic resonance image datasets, the organ structure is already present and segmented or contoured in each case. Accordingly, the outer contour of the organ structure is present and extracted in each case in the multiple training magnetic resonance image datasets.

An option for the further procedure is then to average over the multiple respective outer contours of the organ structure in the training magnetic resonance image datasets, wherein an averaged outer contour of the organ structure is obtained. An inverse Fourier transform can then be carried out, in order to obtain that spatial frequency pattern, the sampling of which results in the averaged outer contour of the organ structure after reconstruction. The spatial frequency pattern can serve as the basis for defining the sampling mask.

Another option for the further procedure is to apply a Fourier transform to the extracted outer contour of the organ structure in the multiple training magnetic resonance image datasets. A signature of the outer contour of the organ structure in the spatial frequency domain is therefore obtained for each training magnetic resonance image dataset. Relevant features of the signature of the outer contour of the organ structure in the spatial frequency domain can then be determined via a Principal Component Analysis (PCA). These can be used as the basis for creating the sampling mask for the concrete case.

In an embodiment, the sampling scheme of k-space supports the subsequent identification of the organ structure by causing a specific emphasizing or a specific saturation of the organ structure to be identified, as compared with surrounding tissue, in the magnetic resonance image data reconstructed from the magnetic resonance measurement data.

The sampling scheme can be selected such that the organ structure appears in the magnetic resonance image data with a particularly high signal as compared with the surrounding tissue, or with the lowest possible signal as compared with the surrounding tissue, or a zero signal. The employment of an inversion recovery sampling scheme, which selectively saturates the tissue of the organ structure as compared with the surrounding tissue, is suitable in this regard. This technique can be employed whenever the organ structure contains fatty tissue, such as the liver. The specific emphasis or specific saturation of the organ structure to be identified makes it possible to simplify identification of the organ structure.

In another embodiment, the sampling scheme of k-space supports the subsequent identification of the organ structure by causing a measurement geometry, specifically coordinated to the organ to be identified, in the magnetic resonance image data reconstructed from the magnetic resonance measurement data.

The measurement geometry can be coordinated to the organ structure to be identified so that the sampling scheme exclusively samples specific slices that are particularly suitable for identification of the organ structure or the outer contour of the organ structure. It is also possible to sample a number of slices that intersect in a region of the organ structure and therefore can provide redundant information along various slice directions in the region of the organ structure. Use of a so-called zoomed imaging method is also conceivable, in which the sampling scheme provides a measurement field (field of view, FOV) that is reduced so as to encompass only, or primarily the region of the organ structure. It can also be beneficial to select a measurement geometry in which changes in the organ structure over time, for example due to a breathing movement of the examined objects, can be detected.

In a further embodiment, the identification of the organ structure involves a segmentation and/or contouring of the organ structure for employment in the course of a radiation treatment of the examined object.

The segmented and/or contoured organ structure can be employed as the target organ or risk organ in planning the radiation treatment of the examined object. Furthermore, it is possible to employ the segmented and/or contoured organ structure when setting up the patient for treatment in the treatment room, e.g. by monitoring the correct positioning of the target organ. A further application is the monitoring of the target organ and/or at-risk organs during the application of the radiation treatment beam. In the latter case the magnetic resonance apparatus advantageously is a part of a combined MR-LINAC apparatus. The magnetic resonance apparatus can also be positioned near the treatment room, in which the LINAC apparatus is installed, with a patient transfer being organized between the magnetic resonance apparatus and the LINAC apparatus. In this manner, the inventive procedure enables acquisition of magnetic resonance image data that are particularly suitable for employment in the course of the radiation treatment of the examined object.

Furthermore, a possible application of the segmented and/or contoured organ structure is the planning and/or preparation and/or monitoring of a MR-guided interventional procedure regarding the organ structure of the patient. The identification of the organ structure can also be used intraoperatively.

In another embodiment, a further acquisition of further magnetic resonance diagnostic measurement data of the organ structure of the examined object is effected by the magnetic resonance apparatus using a further magnetic resonance sequence to operate the scanner, so further magnetic resonance image data are reconstructed from the further magnetic resonance measurement data. The organ structure segmented and/or contoured on the basis of the magnetic resonance image data is compared with the appearance of the organ structure in the further magnetic resonance image data, for the purpose of quality assurance.

The further magnetic resonance measurement data can be acquired at an earlier time or at a later time than the magnetic resonance measurement data. The organ structure segmented and/or contoured on the basis of the magnetic resonance image data can be presented merged with the further magnetic resonance image data for the comparison. It is also possible to compare parameters, such as a volume for example, of the organ structure segmented and/or contoured on the basis of the magnetic resonance image data with the same organ structure segmented and/or contoured on the basis of the further magnetic resonance image data. Those skilled in the art are familiar with further options for comparison.

In this embodiment of the inventive procedure, it is possible to ensure an adequate quality of the magnetic resonance measurement data acquired by the sampling scheme for employment in the course of a treatment of the patient. A visual quality assurance is achieved in this regard with respect to the further magnetic resonance image data, which may be acquired with the use of a conventional sampling scheme. The quality assurance can ensure, for example, that the spatial geometry of the organ structure was not distorted in any relevant manner by the sampling scheme used. Quality assurance of the organ structure segmented and/or contoured on the basis of the magnetic resonance image data is also conceivable with respect to an atlas containing a typical appearance of the organ structure for a population.

The inventive magnetic resonance apparatus has a measurement data acquisition scanner and a computer, wherein the magnetic resonance apparatus is configured to implement the inventive method.

The measurement data acquisition scanner is operated to acquire magnetic resonance measurement data of the organ structure of the examined object using a magnetic resonance sequence that specifies a sampling scheme of k-space. The sampling scheme of k-space supports the subsequent identification of the organ structure in the magnetic resonance image data reconstructed from the magnetic resonance measurement data.

The computer is configured so as to send control signals to the magnetic resonance scanner and/or to receive control signals and/or to process them, in order to implement at least part of the inventive method. The computer can be integrated in to the magnetic resonance apparatus. The computer can also be installed separately from the magnetic resonance apparatus or the scanner thereof. The computer can be connected to the magnetic resonance apparatus. In particular, in order to implement at least part of the inventive method, the computer has a reconstruction unit for reconstructing magnetic resonance image data from the magnetic resonance measurement data and an identification unit for identifying the organ structure in the magnetic resonance image data.

The components of the computer of the inventive magnetic resonance apparatus such as the reconstruction processor or the identification processor can be realized for the most part in the form of software components. These components can also be, especially where particularly rapid calculations are involved, in the form of software-supported hardware components such as FPGAs or the like. The necessary interfaces can likewise be realized as software interfaces, for example when just importing data from other software components is involved. They can also be realized in the form of hardware-based interfaces that are activated by suitable software. It is naturally also conceivable for a number of these components to be realized in combination in the form of a single software component or a software-supported hardware component.

A non-transitory, computer-readable data storage medium according to the invention can be loaded directly into a memory of a programmable computer of a magnetic resonance apparatus and is encoded with program-code as instructions for carrying out the method according to the invention when the program code is executed in the computer. This enables the method according to the invention to be carried out quickly, identically repeatedly and robustly. The computer must meet the requirements for carrying out the respective method steps efficiently, for example have a suitable working memory, a suitable graphics card or a suitable logic board.

Examples of electronically readable data carrier (non-transitory storage medium) are a DVD, a magnetic tape or a USB stick on which electronically readable control information, in particular software (see above), is stored.

The advantages of the magnetic resonance apparatus according to the invention and the storage medium according to the invention substantially correspond to the advantages of the method according to the invention, as explained in detail above. Features, advantages or alternative embodiments noted above are also applicable to the other aspects of the invention. The functional features of the method are achieved by corresponding object modules, in particular by hardware modules in the apparatus.

DESCRIPTION OF THE PREFERRED EMBODIMENTS

Figure 1:
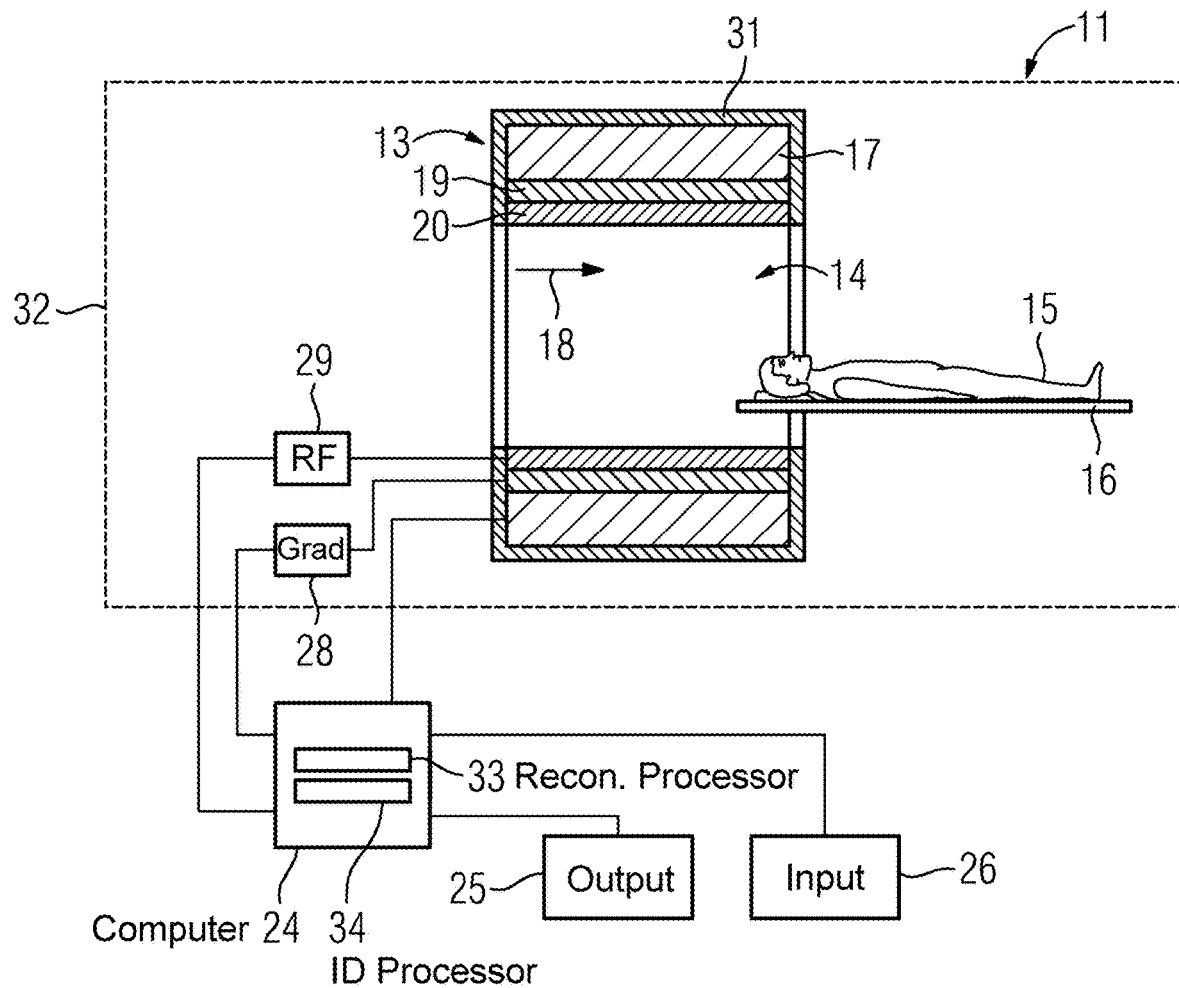
FIG. 1 is a block diagram of an inventive magnetic resonance apparatus.

FIG. 1 schematically illustrates an inventive magnetic resonance apparatus 11. The magnetic resonance apparatus 11 has a scanner 13 having a basic field magnet 17 that generates a strong and constant basic magnetic field 18. The magnetic resonance scanner 13 has a cylindrical patient-receiving region 14 for receiving an examination object 15, in the present case a patient, with the patient-receiving region 14 being cylindrically surrounded in a circumferential direction by the scanner 13. The patient 15 can be moved by a patient-positioning device 16 of the magnetic resonance apparatus 11 into the patient-receiving region 14. The patient-positioning device 16 has for an examination table that is movable inside the scanner 13. The scanner 13 is shielded from the outside by a housing shell 31.

The scanner 13 also has a gradient coil arrangement 19 for generating magnetic field gradients for spatially encoding the magnetic resonance signals. The gradient coil arrangement 19 is controlled by a gradient controller 28. The scanner 13 also has a radio-frequency (RF) antenna 20, which in the illustrated case is designed as a body coil permanently integrated in the scanner 13. The radio-frequency antenna 20 is controlled by a radio-frequency controller 29 so as to radiate radio-frequency magnetic resonance sequences into an examination volume which is formed substantially by the patient-receiving region 14. The radio-frequency magnetic resonance sequence excites certain nuclear spins in the patient 15 so as to deflect the excited nuclear spins from the alignment thereof along the basic magnetic field 18. As those excited nuclear spins relax, they emit magnetic resonance signals, which are also radio-frequency signals. The radio-frequency antenna 20 is also designed to receive the magnetic resonance signals from the patient 15.

For controlling the basic field magnet 17, the gradient controller 28 and the radio-frequency controller 29, the magnetic resonance apparatus 11 has a computer 24. The computer 24 centrally controls the magnetic resonance apparatus 11, such as to execute a predetermined imaging gradient echo sequence. Control information such as imaging parameters, and reconstructed magnetic resonance images can be presented at an output interface 25, in the present case a display monitor, of the magnetic resonance apparatus 11 for a user. The magnetic resonance apparatus 11 has an input interface 26, via which information and/or parameters can be entered by a user during a scanning process. The computer 24 can include the gradient controller 28 and/or radio-frequency controller 29 and/or the output interface 25 and/or the input interface 26.

The computer 24 has a reconstruction processor 33 for reconstructing magnetic resonance image data from the magnetic resonance measurement data and an identification processor 34 for identifying the organ structure in the magnetic resonance image data.

The magnetic resonance apparatus 11 shown can include further components that are normally present in magnetic resonance apparatuses. The general mode of operation of a magnetic resonance apparatus is known to those skilled in the art so a more detailed description of the further components and such operation is not necessary herein.

Figure 2:
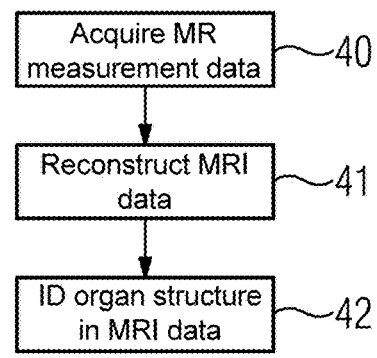
FIG. 2 is shows a flowchart of a first embodiment of the inventive method.

FIG. 2 shows a flowchart of a first embodiment of the inventive method.

In a first method step 40 the scanner 13 of the magnetic resonance apparatus 11 is operated to, acquire magnetic resonance measurement data for an organ structure of the examined object using a magnetic resonance sequence that specifies a sampling scheme of k-space.

In a further method step 41 the reconstruction processor 33 of the computer 24 reconstructs the magnetic resonance image data from the magnetic resonance measurement data.

In a further method step 42 the identification processor 34 of the computer 24 identifies of the organ structure in the magnetic resonance image data.

The sampling scheme of k-space supports the subsequent identification of the organ structure in the magnetic resonance image data reconstructed from the magnetic resonance measurement data.

Figure 3:
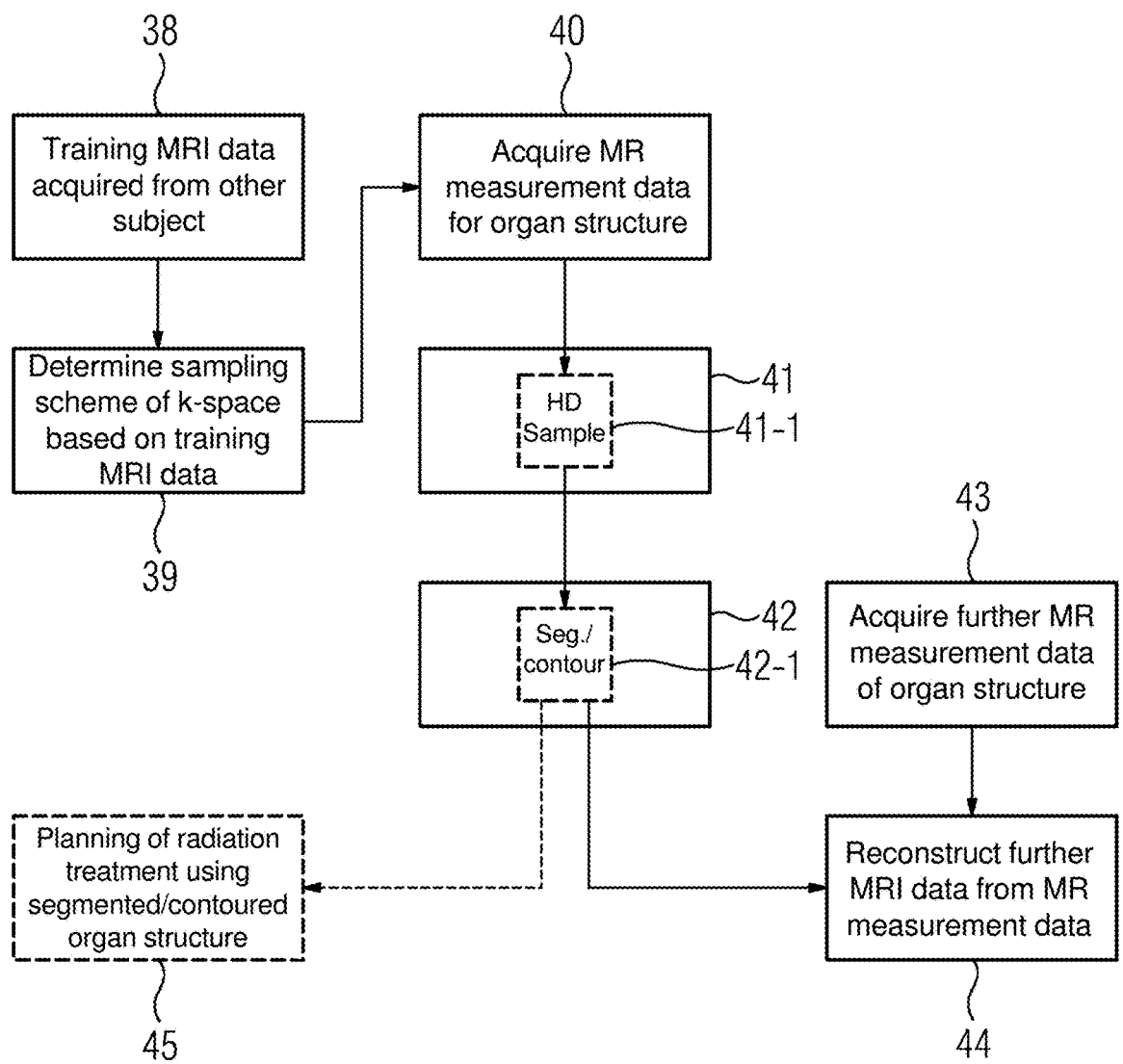
FIG. 3 is a flowchart of a second embodiment of the inventive method.

FIG. 3 shows a flowchart of a second embodiment of an inventive method.

The following description is substantially limited to the differences from the exemplary embodiment in FIG. 2, with reference being made to the description of the exemplary embodiment in FIG. 2 in relation to identical method steps. Method steps that are substantially the same are basically numbered with the same reference numerals.

The embodiment of the inventive method shown in FIG. 3 substantially comprises the method steps 40, 41, 42 of the first embodiment of the inventive method according to FIG. 2. In addition, the embodiment of the inventive method shown in FIG. 3 comprises additional method steps and/or substeps. An alternative procedure to that in FIG. 3, which has only some of the additional method steps and/or substeps shown in FIG. 3, is also conceivable. Of course an alternative procedure to that in FIG. 3 can also have additional method steps and/or substeps.

Figure 4:
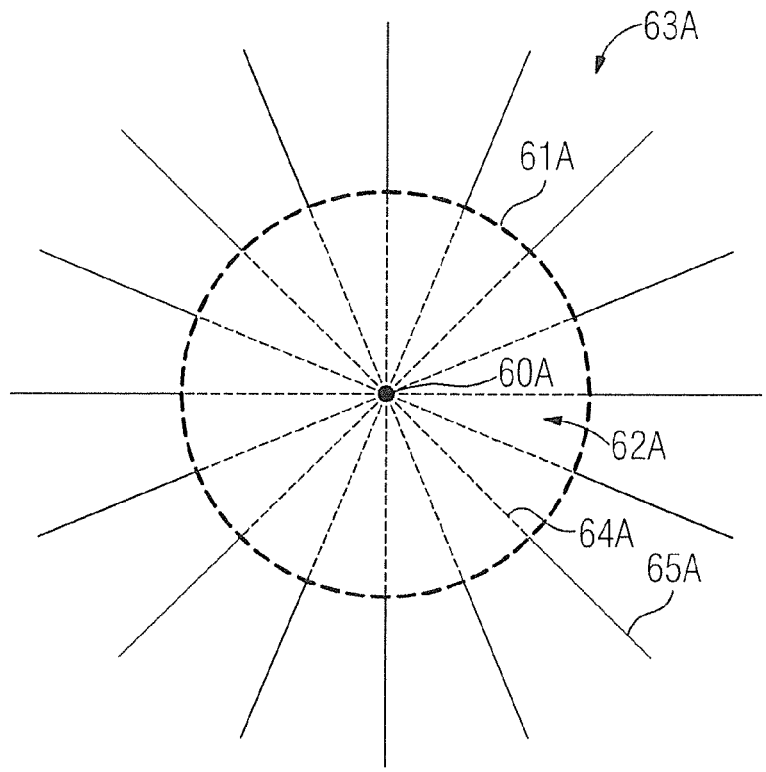
FIG. 4 shows an exemplary radial sampling scheme that supports the subsequent identification of the organ structure.
Figure 5:
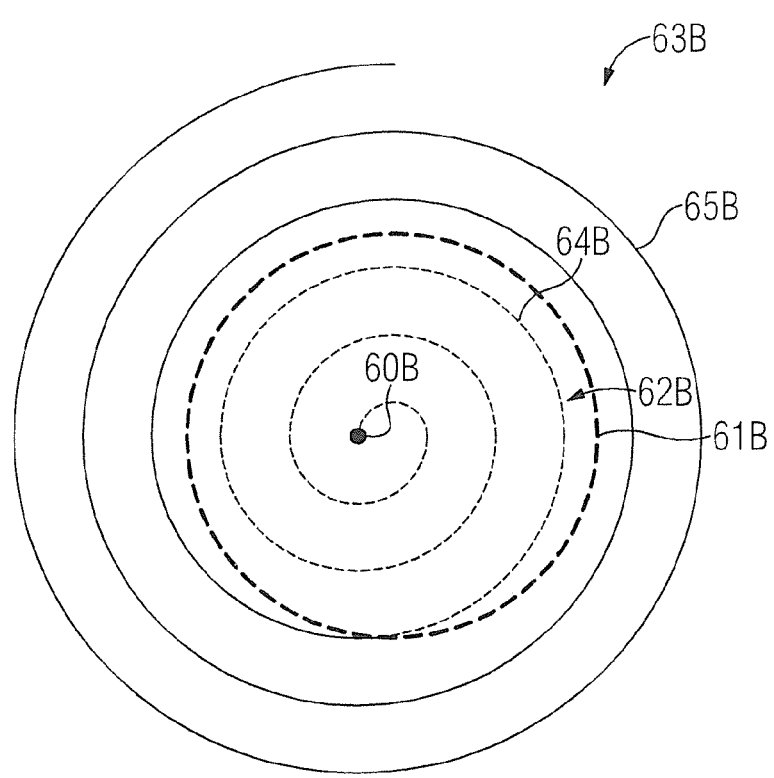
FIG. 5 shows an exemplary spiral sampling scheme that supports the subsequent identification of the organ structure.

There are different possibilities how the sampling scheme of k-space can support the subsequent identification of the organ structure. FIGS. 3-5 show that the sampling scheme of k-space supports the subsequent identification of the organ structure in the manner that the sampling scheme of k-space provides for a higher sampling density in an outer region of k-space than in a central region of k-space.

The higher sampling density in the outer region than in the central region results in an emphasizing of an outer contour of the organ structure in the reconstructed magnetic resonance image data in a substep 41-1 of the method step 41. The identification of the organ structure is effected using the emphasized outer contour of the organ structure in the magnetic resonance image data in a substep 42-1 of the method step 42.

In a further method step 38 training magnetic resonance image data are acquired from at least one subject other than the examined object. The organ structure of the at least one subject is already present and identified in the training magnetic resonance image data. In a further method step 39 the sampling scheme of k-space is determined based on training magnetic resonance image data. This includes a calculation of a sampling mask based on an outer contour of the organ structure of the at least one subject identified in the training magnetic resonance image data, wherein the sampling scheme of k-space provides for a sampling of k-space according to the sampling mask in a manner such that an outer contour of the organ structure of the examined object is emphasized in the reconstructed magnetic resonance image data.

The identification of the organ structure comprises a segmentation and/or contouring of the organ structure in the substep 42-1 of the further method step 42. This segmented and/or contoured organ structure can be employed in the planning of a radiation treatment of the examined object in a further method step 45.

Additionally, a further acquisition of further magnetic resonance measurement data of the organ structure of the examined object can be effected by the magnetic resonance apparatus 11 using a further magnetic resonance sequence in a further method step 43, wherein further magnetic resonance image data are reconstructed from the further magnetic resonance measurement data. In a further method step 44, the organ structure segmented and/or contoured on the basis of the magnetic resonance image data can be compared with an appearance of the organ structure in the further magnetic resonance image data for the purpose of quality assurance.

One other possibility how the sampling scheme of k-space can support the subsequent identification of the organ structure is that the sampling scheme of k-space results in a specific emphasizing or a specific saturation of the organ structure to be identified as compared with surrounding tissue in the magnetic resonance image data reconstructed from the magnetic resonance measurement data.

One other possibility how the sampling scheme of k-space can support the subsequent identification of the organ structure is that the sampling scheme of k-space results in a measurement geometry specifically coordinated to the organ to be identified in the magnetic resonance image data reconstructed from the magnetic resonance measurement data.

The method steps of the method according to the invention shown in FIGS. 2-3 are carried out by the computer. To this end, the computer comprises the necessary software and/or computer programs, which are stored in a memory unit of the computer. The software and/or computer programs comprise program means designed to carry out the method according to the invention when the computer program and/or software is executed in the computer by a processor thereof.

FIGS. 4 and 5 both show exemplary sampling schemes which can support the subsequent identification of the organ structure. Both Figures only show schematic representations of the sampling schemes which only serve an illustrative purpose. Of course, other sampling schemes are possible, e.g. Cartesian sampling schemes or other forms of sub-sampling.

In both Figures the sampling path in k-space is depicted. In this case, k-space is divided into a central region 62A, 62B and an outer region 63A, 63B. The central region 62A, 62B surrounds the center 60A, 60B of k-space. The outer region 63A, 63B surrounds the central region 62A, 62B. The central region 62A, 62B is delimited from the outer region 63A, 63B by a boundary line 61A, 61B. In FIGS. 4-5 the boundary line 61, 61B is a circle. However, any suitable shape can be chosen for the boundary line 61A, 61B between the outer region 63A, 63B and the central region 62A, 62B.

The sampling scheme of k-space provides for a higher sampling density in the outer region 63A, 63B of k-space than in a central region 62A, 62B of k-space. Particularly, the sampling scheme of k-space provides for a sampling of k-space exclusively in the outer region 63A, 63B. Thereby, FIG. 4 shows a radial sampling of k-space exclusively in the outer region 63A. FIG. 5 shows a spiral sampling of k-space exclusively in the outer region 63B.

In the radial sampling shown in FIG. 4 k-space is sampled in several spokes which pass through the center 60A of k-space. A spoke is split into a central part 64A and an outer part 65A. The central part 64A of the spoke lies in the central region 62A of k-space. The outer part 65A of the spoke is positioned in the outer region 63A of k-space. Only the outer part 65A of the spoke is sampled according to the sampling scheme of FIG. 4.

In the spiral sampling shown in FIG. 5 k-space is sampled according to a spiral which originates in the center 60B of k-space. The spiral is split into a central part 64B and an outer part 65B. The central part 64B of the spiral lies in the central region 62B of k-space. The outer part 65B of the spiral is positioned in the outer region 63B of k-space. Only the outer part 65B of the spiral is sampled according to the sampling scheme of FIG. 5.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for identifying an organ structure of an examination subject in magnetic resonance image data, comprising:

operating a magnetic resonance data acquisition scanner to acquire magnetic resonance measurement data from the organ structure of an examination subject, using a magnetic resonance data acquisition sequence that specifies a sampling scheme for k-space to enter said magnetic resonance measurement data into both a central region and an outer region of k-space;

in a reconstruction processor, reconstructing the magnetic resonance image data from the magnetic resonance measurement data entered into k-space;

in an identification processor, identifying the organ structure in the magnetic resonance image data; and specifying said sampling scheme of k-space in said magnetic resonance data acquisition sequence to support said identification of the organ structure in the magnetic resonance image data reconstructed from the magnetic resonance measurement data entered into k-space, said sampling scheme of k-space being configured to produce a higher sampling density in the outer region of k-space than in the central region of k-space, wherein said higher sampling density in said outer region emphasizes an outer contour of the organ structure in the reconstructed magnetic resonance image data, said identifying of said organ structure using the emphasized outer contour of the organ structure in the magnetic resonance image data.

2. A method as claimed in claim 1, wherein said sampling scheme of k-space comprises a spiral sampling or radial sampling of k-space, with a higher sampling density in said outer region than in said central region.

3. A method as claimed in claim 1 wherein said specifying of said sampling scheme of k-space is performed in a processor provided with training magnetic resonance image data acquired from at least one subject other than said examination subject, and in which said organ structure of said at least one subject is already present and identified in said training magnetic resonance image data.

4. A method as claimed in claim 3 comprising determining said sampling scheme of k-space in said processor based on said training magnetic resonance data by calculating a sampling mask based on an outer contour of the organ structure of said at least one subject that is identified in the training magnetic resonance image data, and entering said magnetic resonance measurement data into k-space according to said sampling mask to cause an outer contour of the organ structure of the examination subject to be emphasized in the reconstructed magnetic resonance image data, and identifying said organ structure of the examination subject using the emphasized outer contour of the organ structure in the magnetic resonance image data.

5. A method as claimed in claim 1 wherein said specifying of said sampling scheme of k-space is configured to produce a specific emphasis or a specific saturation of the organ structure, compared with surrounding tissue in the examination subject, in the magnetic resonance image data reconstructed from the magnetic resonance measurement data.

6. A method as claimed in claim 1 wherein said specifying of said sampling scheme of k-space is configured to produce a measurement geometry that is coordinated to said organ to be identified in the magnetic resonance image data reconstructed from the magnetic resonance measurement data.

7. A method as claimed in claim 1 comprising identifying said organ structure by at least one of a segmentation of the organ structure or a contouring of the organ structure in planning a radiation treatment of said examination subject.

8. A method as claimed in claim 7 comprising operating said magnetic resonance data acquisition scanner to acquire further magnetic resonance measurement data of the organ structure of the examination subject using a further magnetic resonance sequence, and reconstructing further magnetic resonance image data from the further magnetic resonance measurement data, and comparing an appearance of said organ structure, obtained by said segmentation or contouring, in the further magnetic resonance image data with the appearance of the organ structure in the magnetic resonance image data, for quality assurance.

9. A method as claimed in claim 1, wherein k-space is sampled along a single trajectory through the outer region and the central region of k-space.

10. A magnetic resonance apparatus comprising:
a magnetic resonance data acquisition scanner; and
a computer including a reconstruction processor and an identification processor, the computer being configured to operate said magnetic resonance data acquisition scanner to acquire magnetic resonance measurement data from an organ structure of an examination subject, using a magnetic resonance data acquisition sequence that specifies a sampling scheme for k-space to enter said magnetic resonance measurement data into both a central region and an outer region of k-space, wherein:
said reconstruction processor is configured to reconstruct magnetic resonance image data from the magnetic resonance measurement data entered into k-space;
said identification processor is configured to identify the organ structure in the magnetic resonance image data; and
said computer is further configured to specify said sampling scheme of k-space in said magnetic resonance data acquisition sequence to support said identification of the organ structure in the magnetic resonance image data reconstructed from the magnetic resonance measurement data entered into k-space, said sampling scheme of k-space being producing a higher sampling density in the outer region of k-space than in the central region of k-space, wherein said higher sampling density in said outer region emphasizes an outer contour of the organ structure in the reconstructed magnetic resonance image data, said identifying of said organ structure using the emphasized outer contour of the organ structure in the magnetic resonance image data.

11. A non-transitory, computer-readable data storage medium encoded with programming instructions, said storage medium being loaded into a computer of a magnetic resonance apparatus, that comprises a magnetic resonance data acquisition scanner, said programming instructions causing said computer to:
operate the magnetic resonance data acquisition scanner to acquire magnetic resonance measurement data from an organ structure of an examination subject, using a magnetic resonance data acquisition sequence that specifies a sampling scheme for k-space to enter said magnetic resonance measurement data into both a central region and an outer region of k-space;
reconstruct magnetic resonance image data from the magnetic resonance measurement data entered into k-space;
identify the organ structure in the magnetic resonance image data; and
specify said sampling scheme of k-space in said magnetic resonance data acquisition sequence to support said identification of the organ structure in the magnetic resonance image data reconstructed from the magnetic resonance measurement data entered into k-space, said sampling scheme of k-space being configured to produce a higher sampling density in the outer region of k-space than in the central region of k-space, wherein said higher sampling density in said outer region emphasizes an outer contour of the organ structure in the reconstructed magnetic resonance image data, said identifying of said organ structure using the emphasized outer contour of the organ structure in the magnetic resonance image data.

* * * * *